(12) United States Patent
Reichow et al.

(10) Patent No.: US 8,315,127 B2
(45) Date of Patent: Nov. 20, 2012

(54) REACTION, PERFORMANCE AND RESPONSE TIME TESTING SYSTEM

(75) Inventors: Alan W. Reichow, Beaverton, OR (US); Joshua K. Hoyt, Portland, OR (US); Ryan Coulter, Beaverton, OR (US)

(73) Assignee: Nike, Inc., Beaverton, OR (US)

( * ) Notice: Subject to any disclaimer, the term of this patent is extended or adjusted under 35 U.S.C. 154(b) by 497 days.

(21) Appl. No.: 11/732,518

(22) Filed: Apr. 2, 2007

(65) Prior Publication Data
US 2009/0129205 A1    May 21, 2009

Related U.S. Application Data

(60) Provisional application No. 60/787,821, filed on Mar. 31, 2006.

(51) Int. Cl.
*G04F 8/00* (2006.01)
*G04F 10/00* (2006.01)
*A63B 67/00* (2006.01)

(52) U.S. Cl. .......................... 368/110; 368/113; 273/445
(58) Field of Classification Search ...... 368/3, 110–113; 273/445–446; 434/258
See application file for complete search history.

(56) References Cited

U.S. PATENT DOCUMENTS

| | | | | |
|---|---|---|---|---|
| 3,698,385 A | * | 10/1972 | Low et al. | 600/558 |
| 3,916,534 A | * | 11/1975 | Riccio | 434/64 |
| 4,006,539 A | * | 2/1977 | Slomski | 434/258 |
| 4,169,592 A | * | 10/1979 | Hall | 463/7 |
| 4,340,223 A | * | 7/1982 | Kuna et al. | 273/445 |
| 4,502,489 A | * | 3/1985 | Alston, Jr. | 600/559 |

(Continued)

FOREIGN PATENT DOCUMENTS

GB    1070469    6/1967

OTHER PUBLICATIONS

International Search Report; PCT app. No. PCT/US07/08093; Apr. 2, 2007; 2 pages.

(Continued)

*Primary Examiner* — Vit W Miska
(74) *Attorney, Agent, or Firm* — Harness Dickey & Pierce, PLC

(57) ABSTRACT

An athletic performance measurement system determines the reaction time, performance time and response time for an athlete to perform an event. A timing processor is in communication with two spaced-apart switches and when the athlete activates the first switch, it sets in motion a system for randomly activating a transducer that alerts the athlete to start the test. The athlete manipulates the first switch in response to detecting the activated transducer while the device measures the time it takes for this activity, thereby defining the athlete's reaction time. Then, the athlete manipulates the spaced apart second switch while the system monitors the time it takes to perform this task, thereby defining the athlete's performance time. The total response time is then calculated by adding the reaction time to the performance time. A testing protocol for performing a plurality of timed tests and averaging the scores is also disclosed.

19 Claims, 5 Drawing Sheets

U.S. PATENT DOCUMENTS

| | | | |
|---|---|---|---|
| 4,728,100 A | | 3/1988 | Smith |
| 5,088,072 A | | 2/1992 | Fitzmorris |
| 5,844,861 A | * | 12/1998 | Maurer .......................... 368/10 |
| 5,901,961 A | * | 5/1999 | Holland, III .................. 273/445 |
| 6,066,105 A | * | 5/2000 | Guillen ......................... 600/595 |
| 6,072,751 A | * | 6/2000 | Kirson et al. ..................... 368/2 |
| 6,110,073 A | | 8/2000 | Saur et al. |
| 6,371,931 B1 | * | 4/2002 | Guillen ......................... 600/595 |
| 7,042,806 B2 | * | 5/2006 | Fox et al. ........................ 368/10 |
| 2005/0159679 A1 | * | 7/2005 | Harbin et al. ................. 600/587 |
| 2005/0168692 A1 | * | 8/2005 | Harbin et al. ................. 351/202 |
| 2006/0252532 A1 | * | 11/2006 | Stovall ........................... 463/30 |

OTHER PUBLICATIONS

Written Opinion of the International Searching Authority; PCT app. No. PCT/US07/08093; Apr. 2, 2007; 3 pages.

Notification of Transmittal of the International Search Report; PCT app. No. PCT/US07/08093; Apr. 2, 2007; 1 page.

Supplemental European Search Report dated Apr. 7, 2011, Application No. 07754593.7-1222, National Phase of PCT Application No. PCT/US2007/008093.

* cited by examiner

REACTION, PERFORMANCE AND RESPONSE TIME TESTING SYSTEM

CROSS REFERENCE TO RELATED APPLICATION

This application claims priority to U.S. provisional patent application Ser. No. 60/787,821, filed on Mar. 31, 2006.

FIELD OF THE INVENTION

This invention relates to a testing system for accurately measuring, recording and tracking the reaction time, performance time and response time of an athlete and the like.

BACKGROUND OF THE INVENTION

Measurement of an athlete's athletic ability has typically been prone to errors and otherwise limited. For example, the 40-yard dash is a timed event that is usually used to measure an athlete's overall speed. Unfortunately, such a measure does not assess the critical skill of quickness in reacting to an event. Moreover, the evaluator usually uses a stopwatch or the like to time the athlete. He or she starts the stopwatch when they first see movement by the athlete and stops the stopwatch when the athlete crosses a line positioned 40-yards from the start. Variations in how and when the evaluator manually starts and stops the stopwatch can seriously compromise the testing results.

Moreover, many athletic performance tests, as well as with most athletic events themselves, requires the athlete to essentially perform two functions. First, detect and react as quickly as possible to some stimulus, such as a visual or auditory signal, and second, perform the athletic feat called on by the test as quickly as possible.

The time it takes to perform the first function is known as the "reaction time," and the time it takes to perform the second function is referred to herein as the "performance time." The total time from start to finish of the complete event is known as the "response time," which is the sum of the "reaction time" and the "performance time."

It can be appreciated that the traditional stopwatch-type testing of a 40-yard dash only measures an athlete's "performance." It offers little insight into isolating any weaknesses between an athlete's "reaction time" vs. "performance time." For example, an athlete that is a very fast runner may have a good "performance time," but may compromise his or her performance by having a poor "reaction time." Similarly, slow runners may have incredibly fast "reaction times," which may make them better candidates for certain athletic events than their faster running, but slower reacting, competitors. Stopwatch times cannot adequately isolate these athletes from the pack.

Systems for testing a person's reaction time have been used with varying degrees of success. In general, these systems have several drawbacks. For example, they are usually not particularly durable or user friendly, thereby limiting their use in some areas such as for on-site athletic performance measurement. Moreover, they tend to be bulky and cannot be easily used to measure a person's reaction time from both hands and feet. Similarly, they are not easily operated as a stand alone device and/or as a device that easily integrates with a computer system, such as a personal computer or the like.

SUMMARY OF THE INVENTION

Accordingly, despite the known athletic performance and reaction time measuring systems, there remains a need for an accurate reaction time measuring system that overcomes these and other drawbacks of the prior systems that will become apparent from the following disclosure.

In one disclose embodiment, the measuring system has a first switch and a second spaced-apart switch secured to a housing. A processor is in communication with these switches and when the athlete activates the first switch, it sets in motion a system for randomly activating a transducer that alerts the athlete to start the test. The athlete must manipulate the first switch in response to detecting the activated transducer while the device measures the time it takes for this activity, thereby defining the athlete's reaction time. Then, the athlete must manipulate the spaced apart second switch while the system monitors the time it takes to perform this task, thereby defining the athlete's performance time. A total response time is then calculated by adding the reaction time to the performance time.

A testing protocol for performing a plurality of timed tests and averaging the scores is also disclosed.

DETAILED DESCRIPTION OF PREFERRED EMBODIMENTS

Figure 3:
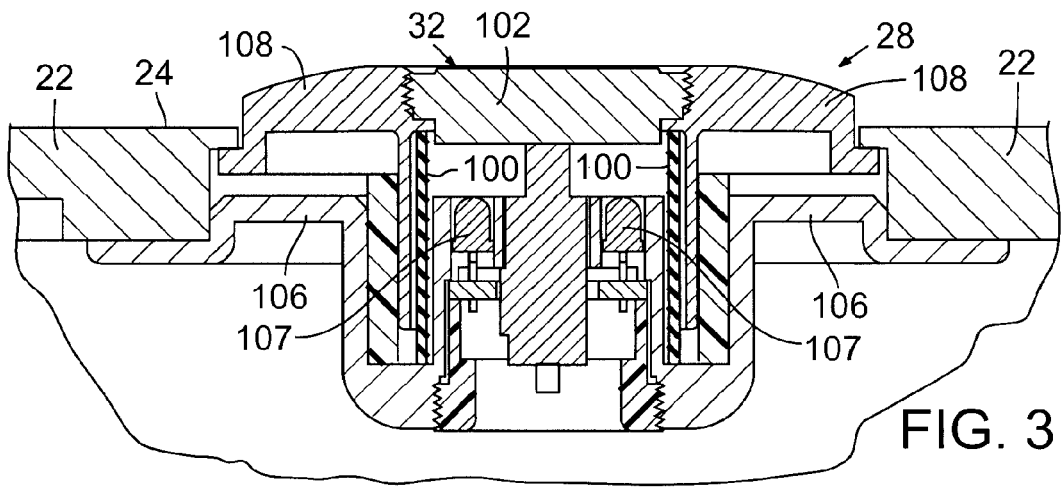
FIG. 3 is a cross-sectional view of a portion of the reaction time testing device of FIG. 1 taken along line 3-3 of FIG. 2A.
Figure 4:
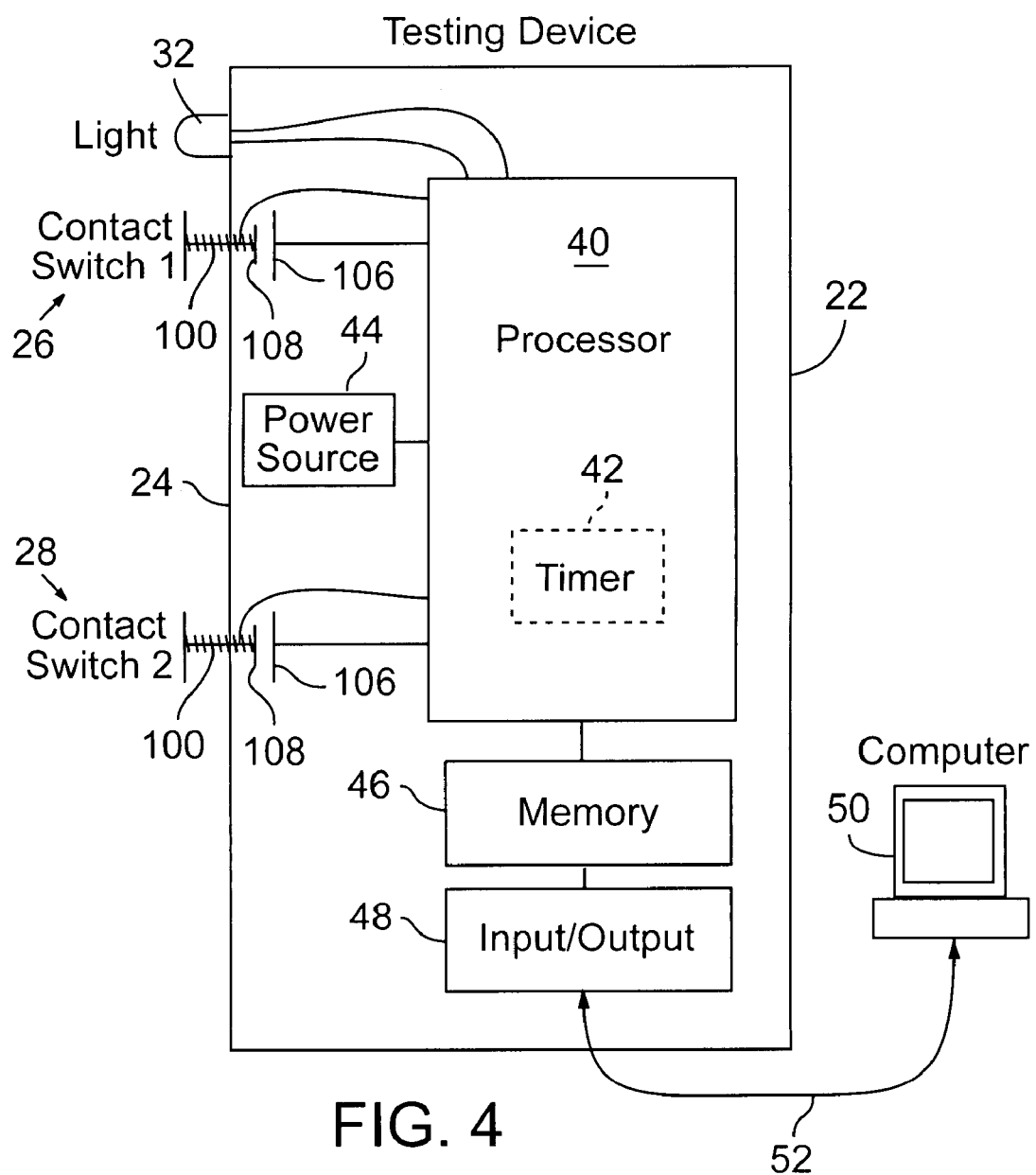
FIG. 4 is a schematic diagram of the reaction time testing device of FIG. 1.
Figure 5:
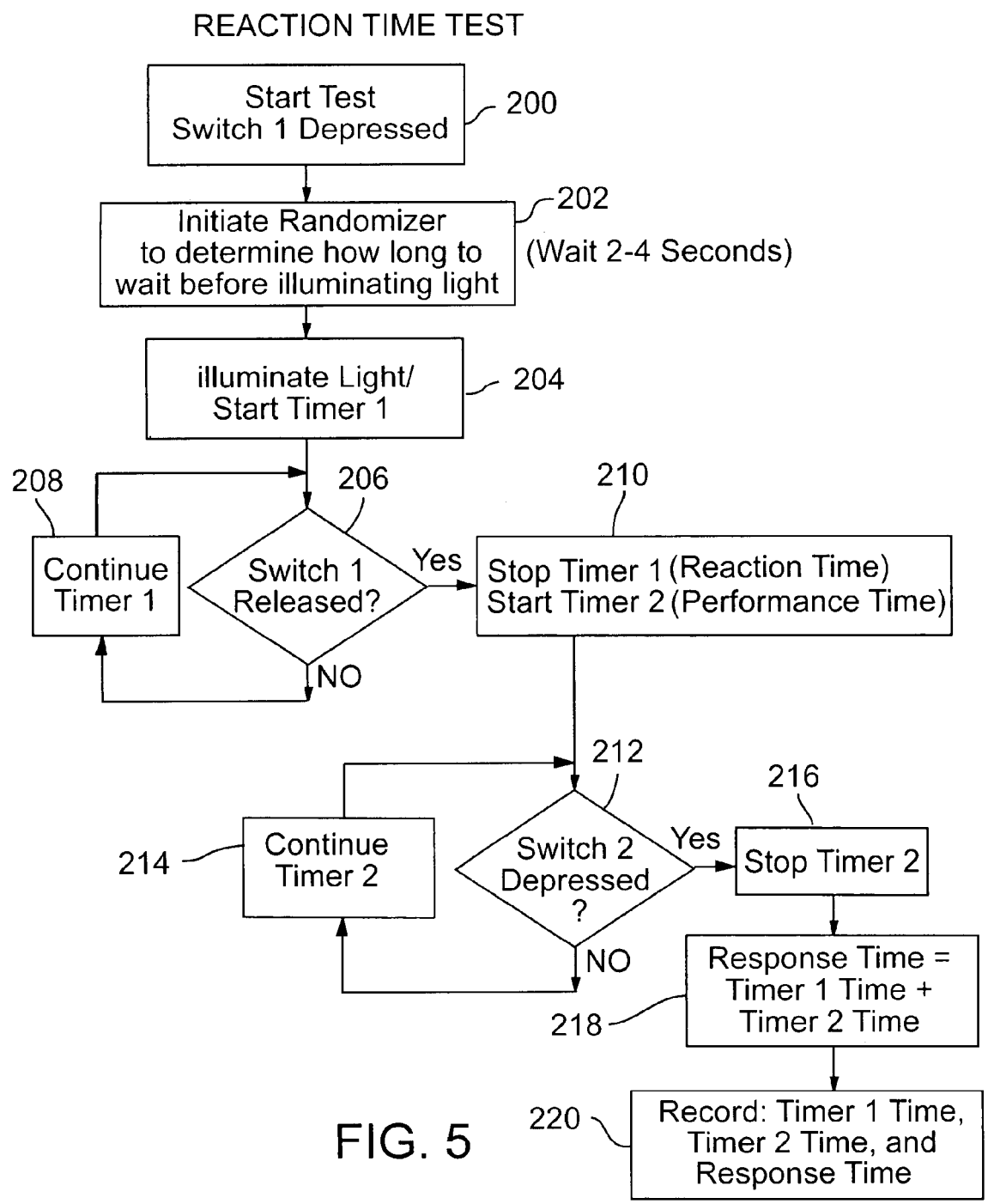
FIG. 5 is a flow diagram of an exemplar test sequence using the reaction time testing device of FIG. 1.
Figure 6:
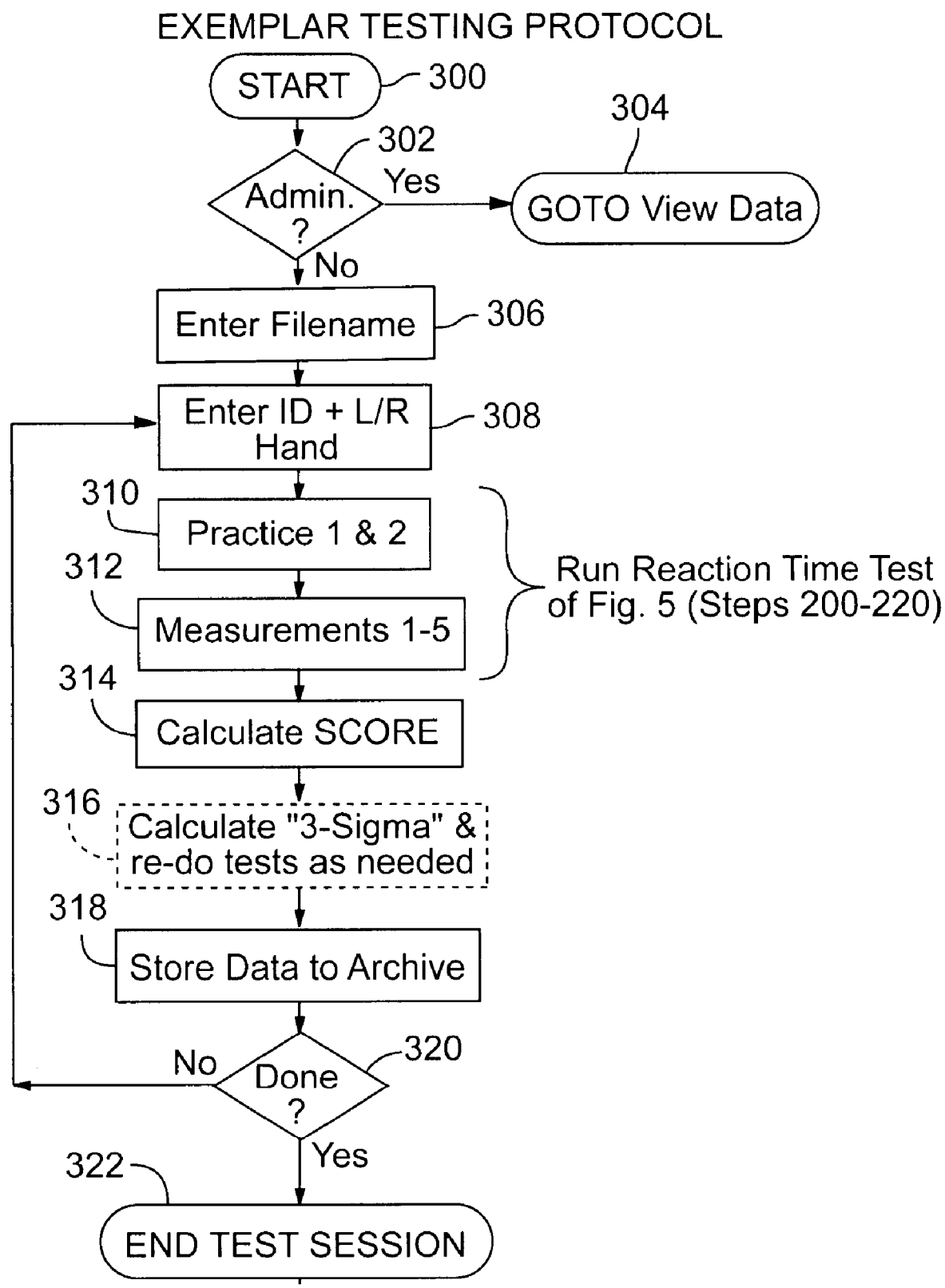
FIG. 6 is a flow diagram of an exemplar session sequence for performing a plurality of the test sequence of FIG. 5 to thereby improve accuracy of the final test results.

A reaction time testing device 20 is disclosed in FIGS. 1-4 & 7-9, and an exemplar method of using the testing device 20 is disclosed in FIGS. 5 & 6.

A. General Assembly

In general and referring to FIGS. 1-4, the testing device 20 preferably has a housing 22 with a substantially planar top surface 24. A first contact switch 26 and a second contact switch 28 are operably secured to the top surface 24 of the housing 22 and spaced apart from each other by a defined distance 30. A transducer 32, such as a signal light, speaker (not shown), or the like is also operably secured to the testing device 22. Preferably, rubber or rubber-like feet 34 (FIG. 2B) are operably secured to the back surface 36 of the housing, thereby allowing the testing device 20 to rest on these feet 34 when placed on a substantially planar surface such as a tabletop or the floor.

Referring to FIG. 4, an exemplar schematic diagram of the testing device 20 is disclosed. The transducer 32, which is preferably a light, first contact switch 26, and second contact switch 28 are all in electrical and operable communication with an internal processor 40. The processor 40 includes traditional control logic and the like for detecting the activation and release of the contact switches 26, 28, and for activating the transducer 32 in accordance with predefined criteria. It also includes a timer 42 for tracking the time of predetermined detected events.

Preferably, the testing device also includes an internal power source 44, memory 46, a data array for correlating the identity of a particular athlete with the test data collected for that athlete, and an input/output device 48 for updating and communicating this and other information between the device 20 and an external computer system 50, such as a laptop or desktop computer or the like.

B. Preferred Device Dimensions and Configuration

Figure 1:
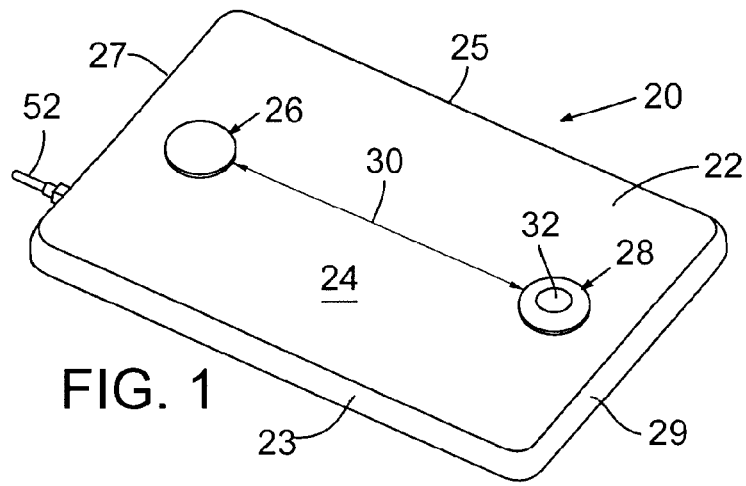
FIG. 1 is a top, left isometric view of a reaction time testing device in accordance with an embodiment of the present invention.

As best shown in FIG. 1, the contact switches 26, 28 are preferably centrally aligned on the top surface 24 of the housing 22, thereby defining a left side 23 and a mirror imaged right side 25. Accordingly, the device 20 can be positioned as needed to test an athlete's left or right hand, or his left or right foot without requiring reconfiguration of the device 20.

Figures 2A, 2B:
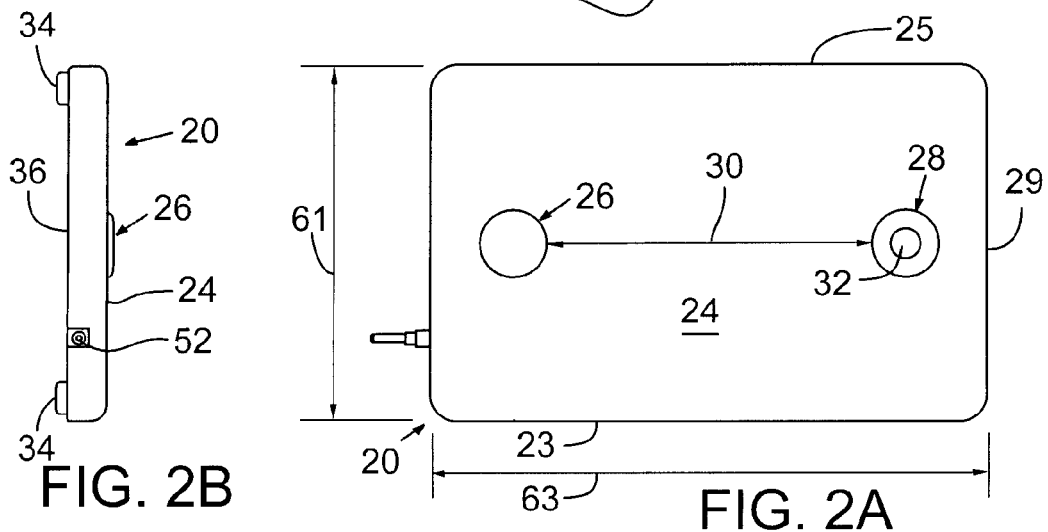
FIG. 2A is a front, plan view of the reaction time testing device of FIG. 1.
FIG. 2B is a top, plan view of the reaction time testing device of FIG. 1.

More preferably, the housing 22 is substantially rectangular-shaped to define a length 63 and a width 61 as best shown in FIG. 2A. The length 63 and width 61 are sized so as to allow the device to work equally well when the athlete uses a hand or foot to activate the test. Known preferable dimensions include a length 63 of about 430 millimeters, and a width 61 of about 44 millimeters. Of course, other dimensions could be used as needed for a particular testing application.

Referring to FIG. 3, the second contact switch 28 and transducer 32 are preferably integrally combined as shown. A central portion 102 of the contact switch 28 is preferably illuminated by diodes 104 positioned immediately below as shown. Spring elements 100 urge the contact switch to a disengaged position as shown in FIG. 3, with switch casing elements 106, 108 maintaining alignment throughout use of the switch. A similar configuration is provided for the first contact switch 26, without the transducer elements imbedded therein.

The device 20 is preferable in direct communication with an auxiliary computer system 50 (FIG. 4). More preferably, the reaction time testing device 20 is a peripheral to a personal computer, and it is configured to accurately measure timing intervals of 1.2 milliseconds (0.0012 seconds). One known processor having an internal timer providing accuracy within this range is manufactured and sold by the Parallax Corporation of Rocklin, Calif. under the part number FT232RL.

Alternatively, the testing device 20 can be configured to be self-contained, thereby allowing remote operation and testing away from the auxiliary computer.

The housing is preferably constructed of light weight, but durable materials such as milled solid aluminum billet, and has a low profile (height), preferably of about 1.5 inches or less. Alternatively, other housing material may be used, such as formed sheet-metal, and the like.

The first and second contact switches are preferably selected from off-the-shelf components designed to be durable and withstand substantial impact.

Figure 7:
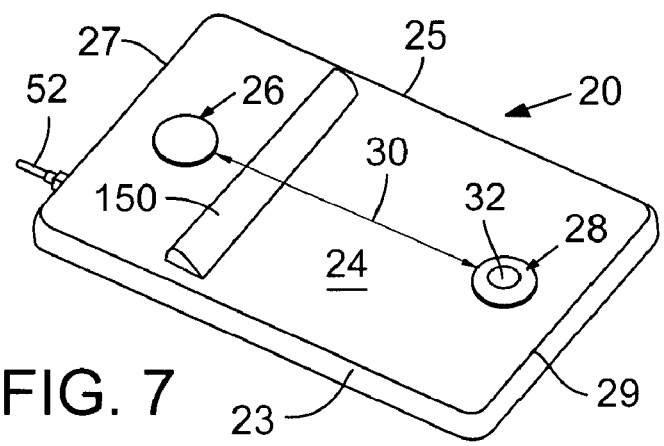
FIG. 7 is a top, left isometric view of an alternative preferred reaction time testing device in accordance with an embodiment of the present invention.
Figures 8A, 8B:
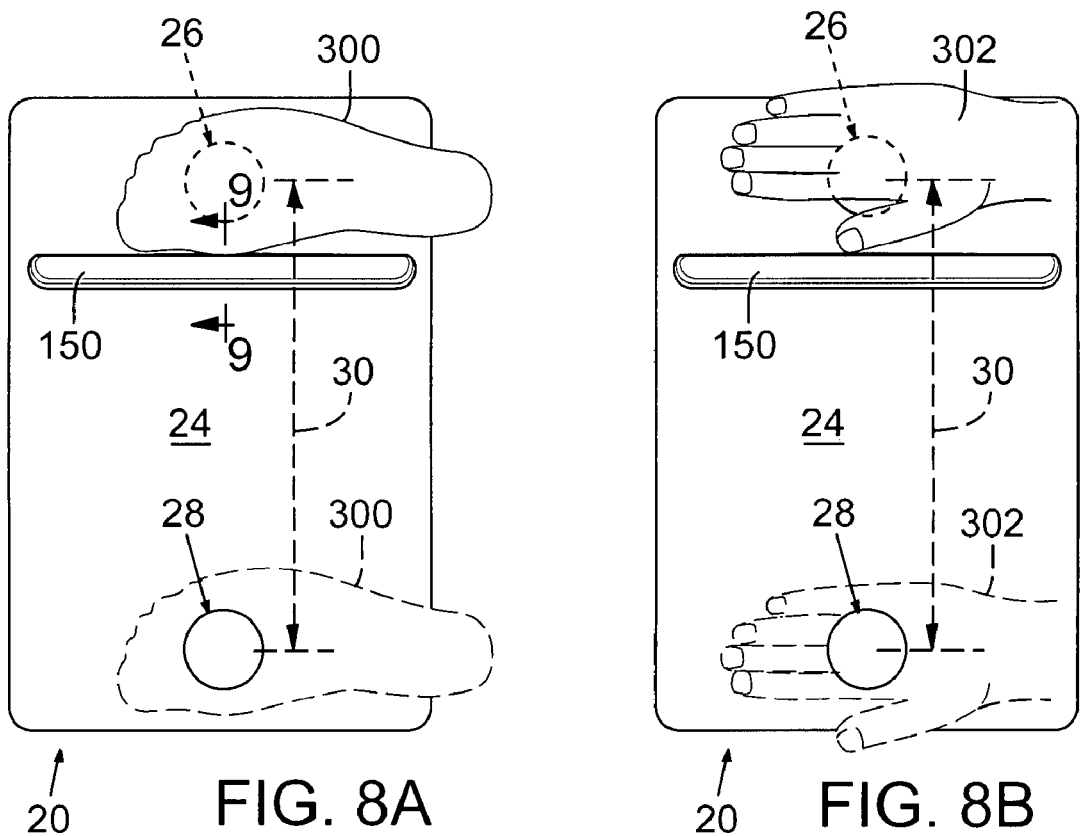
FIG. 8A is a top, plan view of the reaction time testing device showing possible use with an athlete's right foot.
FIG. 8B is a top, plan view of the reaction time testing device showing possible use with an athlete's right hand.

Referring to FIG. 7, if desired, an elongate raised protrusion 150 preferably extends between the first contact switch 26 and the second contact switch 28. As best shown in FIGS. 8A and 8B, this raised protrusion 150 reduces the likelihood of an athlete from simply sliding their hand or foot between the switches during the test without first raising their hand or foot off the first contact switch.

Figure 9:
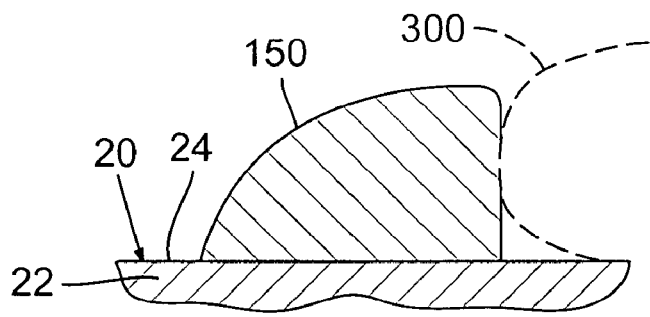
FIG. 9 is an enlarged partial, plan view of the reaction time testing device of FIG. 8A taken along line 9-9 of FIG. 8A.

More preferably, as best shown in FIG. 9, the raised protrusion has a substantially vertical portion positioned adjacent to the athlete's hand or foot when their hand or foot is positioned on the first contact switch 26. The opposite side of the raised protrusion is preferably arcuate as shown to facilitate easy movement toward the second contact switch 28 as best shown in FIGS. 8A and 8B.

C. Reaction Time Test

Referring to FIG. 5, an exemplar reaction time test is disclosed. The test is initiated by the athlete depressing the first contact switch 26 with either their left or right hand (right hand 302 shown in FIG. 8B) or their left or right foot (Right foot 300 shown in FIG. 8A) (Step 200). The depressed and held first contact switch 26 causes the processor 40 (FIG. 4) to initiate an automatic randomizer function (Step 202) thereby randomly selecting a delay time for the test initiating transducer 32 such as the light as shown in FIGS. 1-4 illuminates. This automatic randomizing delay prevents an athlete from gaining an undue advantage from being able to anticipate the start of the test.

Alternatively, the device 20 can include a manual timer adjustment (not shown) that allows the duration before transducer activation to be manually set by the tester.

After waiting the predetermined time, which is preferably between 1 to 5 seconds, and more preferably between 2 to 4 seconds, the processor commands the transducer to illuminate, thereby signaling the start of the test to the athlete. The internal timer is also started (Step 204 at this time. So long as the first contact switch remains depressed by the athlete (Step 206), the timer continues (Step 208). When the athlete releases the first contact switch (Step 206), the timer stops (Step 210), this elapsed time, which is referred to as "timer 1" in FIG. 4, defines the athlete's reaction time, and a second timer is then initiated (Step 210). During this time, the athlete must move their hand or foot that had been actuating the first contact switch to depress the spaced apart second contact switch 28. The second timer continues to run (Step 214) so long as the second contact switch remains un-depressed (Step 212).

When the athlete depresses the second contact switch 28 with their hand 302 (shown in broken lines in FIG. 8B) or foot 300 (shown in broken lines in FIG. 8A) (Step 212), the second timer is stopped (Step 216), thereby defining the performance time of the athlete. The processor then adds the athlete's tested reaction time to his or her performance time (Step 218) to define the athlete's total response time for the test. All three times—reaction time, performance time, and response time are then recorded in the device's memory (step 220).

D. Exemplar Testing Protocol

Referring to FIG. 6, an exemplar testing protocol is disclosed. In general, a plurality of tests is repeatedly performed and the average of these tests is taken to minimize individual errors in a particular test. The testing protocol is initiated (Step 200) by entering an administrative function (Step 302) on the device 20 or more preferably via the auxiliary computer system 50 (FIG. 4) that is in communication with the device 20 during the testing. The auxiliary computer 50 (FIG. 4) preferably includes one or more user interface screens and the like that allow the athlete's name and other testing information to be entered, stored, and modified as needed.

After a particular athlete is identified, a suitable file name for data storage is selected (step 306) and identifying information about the test, such as the user's identification and which hand or foot will be tested, (Step 308) is entered. The protocol then allows the athlete one or more practice tests (Step 310) to become familiar with the testing sequence. Then, the system runs the reaction/performance/response time test of FIG. 5 for a plurality of times (preferably 5) (Step 312) with the results from each test recorded accordingly.

Upon completion of the plurality of tests, the combined scores are calculated (Step 314). Usually, this combined score involves averaging the plurality of test results. However, if desired an error detection algorithm (Step 316) can be included. This error detection algorithm is preferably programmed to analyze the collected data and ignore seriously out of context results, or call for a retest as needed.

After the calculated score is determined, and the resulting data passes the error detection algorithm (if provided), the resulting data is stored in either the devices internal memory, or more preferably in the file name selected in step 306 for future analysis and retrieval through the auxiliary computer system 50 (FIG. 4).

The protocol will then ask if testing is completed (Step 320). If not, the system returns to step 308 for additional testing. Otherwise, the testing session ends (Step 322).

E. Exemplar Athletic Performance Tests

Using the testing device 20 with the test of FIG. 5, and testing protocol of FIG. 6, it can be appreciated that a variety of physical reaction/performance/response time attributes for an athlete can be determined.

For example, eye-hand and eye-foot reaction times (which could also be referred to as "quickness") can be determined, and eye-hand and eye-foot performance times (which could also be referred to as "speed") can be determined. Of course, the traditionally measured total response times for these events can also be determined, but with much more accuracy than had been previously provided through traditional methods and devices.

Exemplar physical tests using the device 20, test sequence, and protocol are set forth below:

Exemplar Test 1

Central Eye-Hand Visual Reaction and Response Speeds

Evaluates:

Visual motor reaction and response times to central visual stimuli based upon visually guided eye-hand motor response (via hand button release and press of lit target (button)). Reaction time is measured as the elapsed time between onset of stimulus light and release of depressed "Reaction" button. Response time is measured as total elapsed time between onset of stimulus light and press of "Response" target button light by subject.

A top view of this test is shown in FIG. 8B. The athlete's hand (right hand 302 is shown) starts by depressing the first contact switch 26. When the signal light in the second contact switch illuminates, the athlete raises their right hand over the protrusion 150 and depresses the second contact switch 28 as quickly as he or she can (the athlete's right hand 302 is shown in broken lines depressing the second contact switch).

It can be appreciated that the athlete's left hand can be tested using the same device 20 simply by rotating the testing device 180 degrees.

Test Distance:
Top of instrument 86.4 cm above floor
Illumination:
Dim room (6-7 foot-candles)
Position:
Standing relaxed. When subject is ready for test to begin he/she will depress the "Reaction" button with the palm of the dominant hand. Hand will be lined up tangent to the alignment ridge (the so-called "Speed Bump") with "Reaction" button under flat of hand at base of fingers. Subject's head aligned vertically over "Response" target button.

Critical Factors:
Body, head, hand alignment. Computer screen and examiner should be positioned to the side with the screen angled away so it is not visible to the subject.

Instructional Set:
"Which hand is your dominant hand?" Adjust instrument to measure performance using the dominant hand. "Position yourself with your head directly over the "Response" target button. "Place your right (or left, depending on dominance) hand on this "Reaction" button so that your hand lies up against this ridge. The "Response" target button will turn off when you depress the "Reaction" button. Within 1-5 seconds the "Response" button will light up again. Move your hand over and depress the lit "Response" button as quickly as possible. The reaction button should lie under the base of your hands as I will demonstrate" The instrument will randomize the "Response" stimulus onset to activate between 2-4 seconds after the athlete depresses the "Reaction" button. Subject will be given 2 practice trials, with a minimum of 5 test trials to follow. Subject will not be told his/her times during the testing sequence.

Record:
Reaction, response and motor response times will be logged and maintained by the computer, with the average and standard deviation calculated. If the standard deviation is outside a given limit, the errant data point(s) will be eliminated and another test trial will need to be conducted.

Test 2

Central Eye-Foot Visual Reaction and Response Speeds

Evaluates:

Visual motor reaction and response times to central visual stimuli based upon visually guided eye-foot motor response (via foot button release and press of lit target (button)). Reaction time is measured as the elapsed time between onset of stimulus light and release of depressed "Reaction" button. Response time is measured as total elapsed time between onset of stimulus light and press of "Response" target button light by subject.

A top view of this test is shown in FIG. 8A. The athlete's foot (right foot 300 is shown) starts by depressing the first contact switch 26. When the signal light in the second contact switch illuminates, the athlete raises their right foot over the protrusion 150 and depresses the second contact switch 28 as quickly as he or she can (the athlete's right foot 300 is shown in broken lines depressing the second contact switch).

It can be appreciated that the athlete's left foot can be tested using the same device 20 simply by rotating the testing device 180 degrees.

Test Distance:
Center of buttons of instrument lie 36 cm in front of a firm-seated chair without armrests. Seat of chair is 46 cm above floor. Anchor chair to floor with adhesive tape.
Illumination:
Dim room (6-7 foot-candles)
Position:
Sitting relaxed. When subject is ready for test to begin he/she will depress the "Reaction" button with his/her dominant foot. Foot will be lined up tangent to the alignment ridge (the so-called "Speed Bump") with "Reaction" button under the ball of the foot. Subject's head aligned directly back from the "Response" target button.

Optional Test Set-Up:

Subject is standing with non-dominant foot on floor and tangent to edge of test device nearest the "Response" button. He/she will depress the "Reaction" button with his/her dominant foot.

Critical Factors:

Body, head, hand alignment. Computer screen and examiner should be positioned to the side with the screen angled away so it is not visible to the subject.

Instructional Set:

"Which hand is your dominant foot?" Adjust instrument to measure performance using the dominant foot. "Position yourself with your head directly behind the "Response" target button. "Place your right (or left, depending on dominance) foot on this "Reaction" button so that your foot lies up against this ridge. The "Response" target button will turn off when you depress the "Reaction" button. Within 1-5 seconds the "Response" button will light up again. Move your foot over and depress the lit "Response" button as quickly as possible. The reaction button should lie under the ball of your foot as I will demonstrate" The instrument will randomize the "Response" stimulus onset to activate between 2-4 seconds after the athlete depresses the "Reaction" button. Subject will be given 2 practice trials, with a minimum of 5 test trials to follow. Subject will not be told his/her times during the testing sequence.

Record:

Reaction, response and motor response times will be logged and maintained by the computer, with the average and standard deviation calculated. If the standard deviation is outside a given limit, the errant data point(s) will be eliminated and another test trial will need to be conducted.

In addition to the other benefits of the disclosed testing device 20 and related test methods and protocol, it can be appreciated that the device 20 allows for consistent results to be obtained between different athletes and even between different test administrators. Moreover, so long as the testing devices 20 are constructed substantially similar to each other with the defined distant 30 and related dimensions being substantially similar, consistent results may also be obtained using different testing devices 20, thereby allowing test results to be normalized between different athletes using different, but substantially similar, test devices 20.

As a result, test results can be compared between athletes or normalized between groups of athletes to allow a particular athlete to compare his or her individual results with either their own earlier measured results, with those of other athletes and even with world-class athletes in a particular field who have also performed the testing.

If desired, the computer system can be in communication with the World Wide Web and share this information globally. Also, a particular athlete's testing scores and information may be secured via electronic or other means to prevent its disclosure to third parties.

Having described and illustrated the principles of our invention with reference to a preferred embodiment thereof, it will be apparent that the invention can be modified in arrangement and detail without departing from such principles. For example, although the disclosed transducer is preferably a light, an alternative and/or additional transducers such as a speaker, or a plurality of lights and/or speakers may be used, with each transducer providing a unique testing signal to the athlete as needed.

In view of the many possible embodiments to which the principles may be put, it should be recognized that the detailed embodiments are illustrative only and should not be taken as limiting the scope of our invention. Accordingly, we claim as our invention all such modifications as may come within the scope and spirit of the following claims and equivalents thereto.

We claim:

1. An athletic performance testing system having:
   a moveable discrete housing;
   a processor with a timing element therein operably secured to said discrete housing;
   a first switch operably secured to the discrete housing and manually actuatable by an athlete along a defined plane;
   a second switch operably secured to the discrete housing and manually actuatable by the athlete along the defined plane, said second switch spaced apart from said first switch by a defined distance such that said first switch and said second switch remain spaced apart by the defined distance when said discrete housing is moved;
   a protrusion between said first and second switches extending from the defined plane such that the athlete must traverse the protrusion when transitioning from actuating the first switch to actuating the second switch;
   a transducer operably secured to said housing;
   said first switch, second switch and transducer operably communicating with said processor so that the timer activates upon predetermined criteria involving a random delay time prior to activation of said transducer and one of said the athlete manually manipulating at least one of said first switch and said second switch to determine a timed event.

2. The testing system of claim 1, wherein said predetermined criteria includes timing the time between activation of the transducer and the athlete releasing said first switch to define the timed event as the athlete's reaction time.

3. The testing system of claim 2, wherein said predetermined criteria includes timing the time between the athlete releasing said first switch and activating said second switch to define the athlete's performance time.

4. The testing system of claim 3, wherein said processor calculates a response time by adding said athlete's reaction time with said athlete's performance time.

5. The testing system of claim 1, further including memory operably secured to said processor for storing a result of said timed event.

6. The testing system of claim 1, wherein said discrete housing is substantially planar thereby allowing said discrete housing to rest on a substantially planar surface.

7. The testing system of claim 1, wherein said first switch and said second switch are aligned along a longitudinal centerline of said discrete housing thereby defining a left side and a right side of said discrete housing with said left side being a substantial mirror image of said right side.

8. The testing system of claim 1, wherein said system is in communication with an auxiliary computer.

9. The testing system of claim 8, wherein said auxiliary computer system includes a user interface for entering athlete identifying information and displaying test results obtained from said system.

10. The testing system of claim 1, wherein said transducer is a light.

11. The testing system of claim 10, wherein said light is operably received within said second switch.

12. The testing system of claim 1 wherein said protrusion has a substantially vertical wall positioned toward said first switch.

13. A method for determining the reaction time, performance time and response time of an athlete using a timing device that has two spaced apart switches operably secured within a defined plane of a moveable, discrete housing such that the switches remain spaced apart from each other by a defined distance as the discrete housing is moved, a protrusion positioned between two spaced apart switches and extending from the defined plane, and a transducer in communication with a computer system, said method comprising the steps of:
- depressing one of the two spaced apart switches to activate the test;
- the computer system randomly delaying the activation of the transducer to alert the athlete that the test has started and the computer system initiating a first timer when activating the transducer;
- releasing said one of the two spaced apart switches thereby stopping said first timer to define a reaction time;
- the computer system starting a second timer when said one of the two spaced apart switches is released;
- traversing from the first of said one of two spaced apart switches over the protrusion to the other of said one of two spaced apart switches;
- depressing the other of said two spaced apart switches thereby stopping said second timer to define a performance time;
- the computer system adding said reaction time to said performance time to define a response time.

14. The method for determining reaction time, performance time and response time of an athlete of claim 13, further including the step of writing said reaction time, said performance time and said response time to memory.

15. The method for determining reaction time, performance time and response time of an athlete of claim 14, further including displaying said reaction time, said performance time and said response time on a computer display.

16. The method for determining reaction time, performance time and response time of an athlete of claim 13, wherein said transducer is a light and said two spaced apart switches are contact switches.

17. The method for determining reaction time, performance time and response time of an athlete of claim 13, wherein said first and second switches are substantially centrally aligned on said discrete housing thereby allowing the testing device to be used with to test either an athletes left or right hands.

18. The method for determining reaction time, performance time and response time of an athlete of claim 13, wherein said discrete housing is substantially planar that said discrete housing may rest on either a floor or table, thereby allowing the testing device to be used to test either an athlete's eye-hand reaction time or an athlete's eye-foot reaction time.

19. The method for determining reaction time, performance time and response time of an athlete of claim 13, wherein said method is performed a plurality of times with the average of each said reaction time, performance time and response time being determined.

* * * * *